(12) United States Patent  
Bastide et al.

(10) Patent No.: US 8,558,695 B2  
(45) Date of Patent: Oct. 15, 2013

(54) BIODEGRADABLE DEVICE AND MESH NETWORK FOR OPTIMIZATION OF PAYLOAD MATERIAL DELIVERY

(75) Inventors: Paul Roger Bastide, Boxford, MA (US); Matthew E. Broomhall, South Burlington, VT (US); Robert Edward Loredo, North Miami Beach, FL (US)

(73) Assignee: International Business Machines Corporation, Armonk, NY (US)

( * ) Notice: Subject to any disclaimer, the term of this patent is extended or adjusted under 35 U.S.C. 154(b) by 519 days.

(21) Appl. No.: 12/940,095

(22) Filed: Nov. 5, 2010

(65) Prior Publication Data

US 2012/0116580 A1    May 10, 2012

(51) Int. Cl.
G08B 21/00    (2006.01)

(52) U.S. Cl.
USPC .............. 340/540; 340/539.1; 340/573.1; 340/825.69; 700/240

(58) Field of Classification Search
USPC .......... 340/540, 539.1, 573.1, 825.69, 10.1, 340/10.4; 700/240, 241; 702/2, 4; 705/5; 709/201; 324/71, 71.1
See application file for complete search history.

(56) References Cited

U.S. PATENT DOCUMENTS

| | | |
|---|---|---|
| 5,033,397 A | 7/1991 | Colburn, Jr. |
| 6,070,539 A | 6/2000 | Flamme et al. |
| 6,091,997 A | 7/2000 | Flamme et al. |
| 6,745,128 B2 | 6/2004 | Hanson |
| 6,813,544 B2 | 11/2004 | Hood et al. |
| 7,183,779 B2 * | 2/2007 | Hughes ................. 324/696 |
| 7,492,254 B2 | 2/2009 | Bandy et al. |
| 7,492,326 B1 | 2/2009 | Bodlovic et al. |
| 2005/0149235 A1 * | 7/2005 | Seal et al. ............ 700/283 |
| 2007/0289207 A1 * | 12/2007 | May et al. ............ 47/17 |
| 2009/0204250 A1 | 8/2009 | Potyrailo et al. |
| 2009/0212918 A1 | 8/2009 | Bandy et al. |

* cited by examiner

Primary Examiner — Hung T. Nguyen
(74) Attorney, Agent, or Firm — D'Ambrosio & Menon, PLLC (57) ABSTRACT

A biodegradable payload material delivery and notification device includes a biodegradable shell enclosing at least a portion of a biodegradable detector that includes a payload material, and biodegradable circuitry electrically connected to the detector and capable of performing a delivery notification operation. The biodegradable shell degrades upon exposure to environmental conditions causing release of an amount of the payload material, and the detector communicates release of the amount of the payload material to the circuitry causing the circuitry to perform the delivery notification operation. The delivery notification operation includes generating and transmitting to a mesh network a signal having one or more parameters that are correlated with the amount of the payload material released. A mesh network includes a plurality of biodegradable devices and one or more edge collection devices. Each biodegradable device is configured to broadcast a signal that may be received and processed by the edge collection devices.

20 Claims, 5 Drawing Sheets

BIODEGRADABLE DEVICE AND MESH NETWORK FOR OPTIMIZATION OF PAYLOAD MATERIAL DELIVERY

BACKGROUND

Increasing and optimizing agricultural yields is a matter of tremendous importance in the agricultural industry. Combinations of various substances such as pesticides, herbicides, and fertilizers are typically used to improve agricultural yields. Fertilizers are substances that are used to supplement the natural nutrient supply of a soil to increase its agricultural yield. Fertilizers generally contain, in varying proportions, the primary macronutrients nitrogen, phosphorus, and potassium and the secondary macronutrients calcium, sulfur, and magnesium. Fertilizers also generally include various other micronutrients in lesser proportions.

SUMMARY

Systems, methods, and computer-readable media for collecting and analyzing data relating to payload material delivery are disclosed herein.

In accordance with one or more embodiments of the invention, a biodegradable payload material delivery and notification device comprises: a biodegradable shell enclosing at least a portion of a biodegradable detector that comprises a payload material, and biodegradable circuitry electrically connected to the detector and capable of performing a delivery notification operation. At least a portion of the biodegradable shell may degrade upon exposure to one or more environmental conditions causing release of an amount of the payload material and the detector may communicate release of the amount of the payload material to the circuitry causing the circuitry to perform the delivery notification operation. The delivery notification operation may comprise generating and transmitting to a mesh network a signal having one or more parameters associated therewith that are correlated with the amount of the payload material released.

The biodegradable payload material delivery and notification device may further comprise a plurality of biodegradable conductive leads. The detector may comprise two or more of the plurality of conductive leads and may be electrically connected to the circuitry via the two or more conductive leads. The payload material may be disposed in proximity to the two or more conductive leads of the detector. At least a portion of the conductive leads in the detector may be exposed upon release of the amount of the payload material and the exposed portion of the conductive leads may be brought into contact with one another under a tension force acting on the leads. The circuitry may perform the delivery notification operation in response to a signal received from the detector indicating release of the amount of the payload material, the signal being generated upon contact of the at least a portion of the conductive leads.

Each biodegradable device may further comprise: a biodegradable power source connected to the circuitry via one or more of the plurality of conductive leads, and a biodegradable antenna connected to the circuitry via one or more of the plurality of conductive leads.

In one or more specific embodiments of the invention, the one or more environmental conditions may comprise at least one of: one or more chemical compounds present in a soil of, one or more chemical compounds present in a gaseous atmosphere of the environment in which the biodegradable device is disposed, decomposition of a mass of the payload material, and a water content in the soil of the environment.

In one or more embodiments of the invention, a mesh network comprises: a plurality of biodegradable devices networked together in accordance with a mesh topology, and one or more edge collection devices. Each biodegradable device is configured to transmit a signal to one or more other biodegradable devices in the mesh network. The signal may comprise a data packet having a plurality of data bits that includes a first set of data bits that stores an origin identifier and a second set of data bits that stores one or more hop identifiers. The edge collection devices may receive one or more signals from one or more of the plurality of biodegradable devices and process information included in the received signals.

In one or more embodiments of the invention, a method for collecting and processing payload material delivery data comprises: establishing a mesh network comprising a plurality of biodegradable devices and one or more edge collection devices, configuring each biodegradable device to transmit a signal to one or more other biodegradable devices in the mesh network, the signal comprising a data packet having a plurality of data bits that includes a first set of data bits that stores an origin identifier and a second set of data bits that stores one or more hop identifiers, configuring the edge collection devices to receive one or more signals from one or more of the plurality of biodegradable devices, and configuring the edge collection devices to process information included in the received signals.

Each biodegradable device in the mesh network may be a biodegradable payload material delivery and notification device in accordance with one or more previously disclosed embodiments of the invention.

The origin identifier may be associated with and may provide information representing a location of a device that released the amount of the payload material and that generated and initially transmitted to the mesh network the signal comprising the data packet as part of the delivery notification operation, and each of the hop identifiers may be associated with and may provide information representing a location of a biodegradable device that received the signal comprising the data packet.

In one or more specific embodiments of the invention, the circuitry of each biodegradable device in the mesh network may be capable of performing one or more additional operations comprising: a signal receive operation in which the circuitry determines that a signal transmitted from another biodegradable device has been received by the antenna, and a signal repeat operation in which the circuitry controls the antenna to re-transmit a signal received from another biodegradable device.

The circuitry of a first device in the mesh network may perform the signal repeat operation upon determining, as part of the signal receive operation, that a signal comprising a data packet has been received from a second device in the mesh network. The signal repeat operation may comprise: determining whether a first condition is satisfied, the first condition being satisfied if the second set of data bits of the data packet comprises an identifier associated with the first device among the stored hop identifiers, and discarding the data packet if the first condition is satisfied. If the first condition is not satisfied, a determination may be made as to whether a second condition is satisfied, the second condition being satisfied if the data packet comprises a sufficient number of available data bits for storing the identifier associated with the first device as a hop identifier. If the second condition is satisfied, the signal repeat operation may further comprise: storing the identifier associated with the first device among the available data bits of the data packet to generate a modified data packet and transmitting a signal comprising the modified data packet. If the second condition is not satisfied, the signal repeat operation may further comprise: re-transmitting the signal comprising the data packet.

One or more embodiments of the invention relate to a computer-readable medium that stores a program comprising instructions for: configuring and causing each biodegradable device in a mesh network to transmit a signal to one or more other biodegradable devices in the mesh network, the signal comprising a data packet having a plurality of data bits that includes a first set of data bits that stores an origin identifier and a second set of data bits that stores one or more hop identifiers, configuring and causing edge collection devices of the mesh network to receive one or more signals from one or more biodegradable devices, and configuring and causing the edge collection devices to process information included in the received signals.

In one or more additional embodiments of the invention, a computer-readable medium stores a computer program that comprises a set of instructions for causing the circuitry of a biodegradable device in a mesh network, according to any of the previously disclosed embodiments, to selectively perform one of the delivery notification operation, the signal receive operation, and the signal repeat operation.

These and other embodiments of the invention are described in further detail through reference to the following drawings in the detailed description that follows.

DETAILED DESCRIPTION

As will be appreciated by one of ordinary skill in the art, embodiments of the present invention may comprise a system, method and/or computer program product. Accordingly, embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the present invention may take the form of a computer program product embodied in one or more computer readable medium(s) having computer readable program code embodied thereon.

Any combination of one or more computer readable media may be utilized. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage media would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

Computer program code for carrying out operations for embodiments of the present invention may be written in any combination of one or more programming languages, including, but not limited to, an object oriented programming language such as Java, Smalltalk, C++ or the like, a common language infrastructure (CLI) language such as C#, C++/CLI, F#, J#, #Smalltalk, or any other CLI implementation of another programming language, and/or "conventional" procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Embodiments of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose.

Biodegradability, as used herein, may be defined in accordance with any standard or definition generally accepted by those of ordinary skill in the art.

Figure 1A:
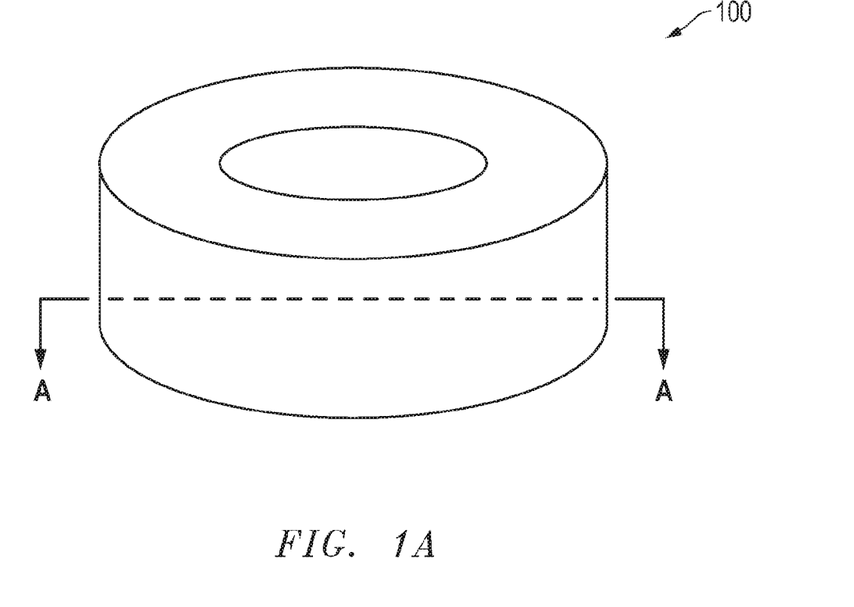
FIG. 1A is a perspective view of a biodegradable device in accordance with one or more embodiments of the invention.
Figure 1B:
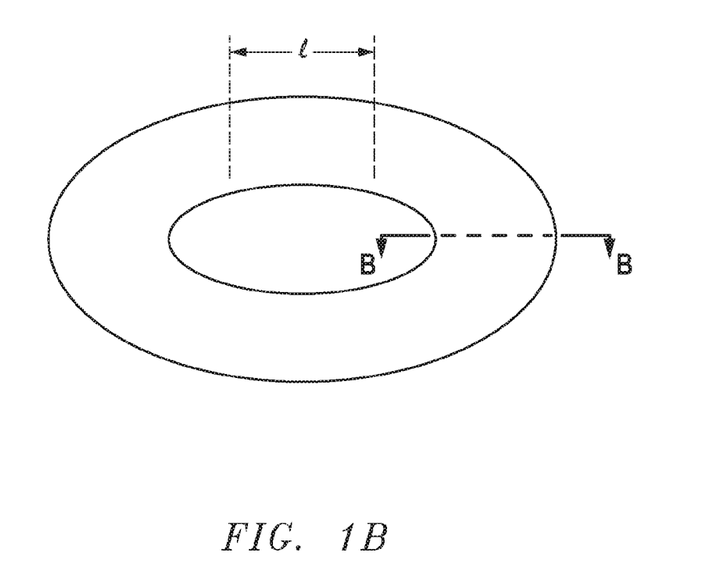
FIG. 1B is a top view of the biodegradable device depicted in FIG. 1A in accordance with an embodiment of the invention.

FIG. 1A depicts a perspective view of a biodegradable device 100 in accordance with an embodiment of the invention. FIG. 1B depicts a top view of the device 100 depicted in FIG. 1A. Components of the device 100 will be described in more detail through reference to the various views depicted in FIGS. 2A-2C.

Figure 2A:
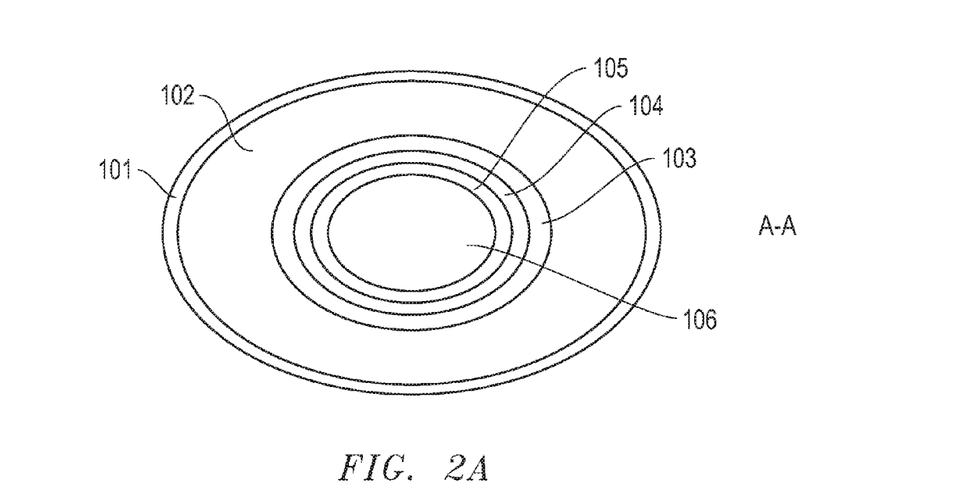
FIG. 2A is a cross-section of the biodegradable device depicted in FIGS. 1A-1B taken along cutting line A-A.

FIG. 2A depicts a cross-sectional view of the biodegradable device 100 shown in FIGS. 1A-1B, the cross-section being taken along cutting line A-A. The device 100 comprises a biodegradable shell 101 that encloses a region 102 of the device 100 that includes at least a portion of a biodegradable detector and at least a portion of biodegradable device circuitry. In certain embodiments of the invention, the biodegradable shell 101 may entirely encompass or enclose the other components of the device. Alternatively, in other embodiments of the invention, a portion of the detector and/or the device circuitry or other device components may be at least partially exposed beyond the shell.

The device 100 may further comprise: an inner frame 104 that provides physical support for one or more other components of the device 100, a biodegradable power source 105 such as a biodegradable battery which may be formed as a layered flat component, and an antenna 103 for transmitting signals to and receiving signals from other biodegradable devices. The antenna 103 may be formed, for example, of a silver filament and may be disposed in a series of coils around the inner frame 104. At least a portion of the inner frame 104 may be in physical contact with the biodegradable power source 105 and/or the antenna 103. The frame 104 may be molded into the shape of disk or any other suitable shape. A hollow center portion 106 may be provided in the device 100 to generate an echo chamber for transmission and reception of signals by the antenna 103. Although the device 100 is shown in FIGS. 1A-1B and 2A as including a hollow center portion 106, in one or more embodiments of the invention, the device may be formed as a solid body without a hollow center portion.

The device circuitry, at least a portion of which is included in region 102 of the device 100, may be formed of biodegradable polymers and resins. Examples of such biodegradable polymers include, but are not limited to, aliphatic polyesters such as polylactic acid, starch derivatives, cellulose esters such as cellulose acetate and nitrocellulose and derivatives thereof, and polyhydroxyalkanoates such as poly-3-hydroxybutyrate (PHB), polyhydroxyvalerate (PHV), and polyhydroxyhexanoate (PHH). The polymers may be formed into a multi-layer laminate structure with each layer fused together with a resin such as a silver paste. The device circuitry may be formed to produce a logical circuit configured to and capable of performing one or more device operations. The operations capable of being performed by the circuitry will be described in greater detail hereinafter.

The biodegradable device 100 may additionally include a plurality of biodegradable conductive leads. The conductive leads may be formed of silver, graphene, carbon nanotubes, or any other metallic/conductive material. Each of the power source 105, the antenna 103, and the detector included in region 102 may be in electrical communication with the device circuitry through at least a portion of the plurality of conductive leads. The device circuitry manages the transmission and reception of signals by the antenna 103 by way of the electrical communication established between the antenna 103 and the device circuitry via one or more of the conductive leads. In certain embodiments, the device circuitry may refer to the laminate structure of biodegradable polymers and resins together with the plurality of conductive leads. In other embodiments, the device circuitry may refer to only the multi-layered laminate structure.

Figure 2B:
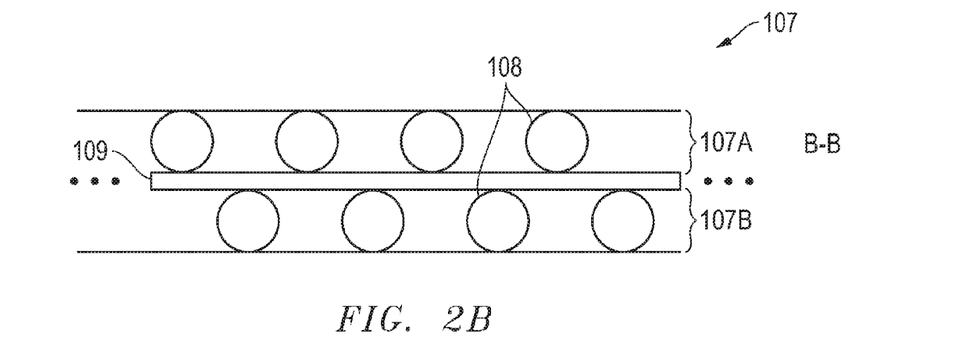
FIG. 2B is a cross-section of at least a portion of the detector of the biodegradable device depicted in FIGS. 1A-1B taken along cutting line B-B.

FIG. 2B depicts a cross-sectional view of at least a portion of the detector 107 included in the region 102 of device 100 depicted in FIGS. 1A-1B, the cross-section being taken along cutting line B-B. The cross-section taken may represent a cross-section across an entire height of the device 100 and/or an entire distance from the hollow center to the outer shell, or may be a partial cross-section of the device 100.

Referring to FIG. 2B, the detector 107 may include two or more of the plurality of conductive leads included in the device 100. The conductive leads 108 that form part of the detector 107 may be arranged concentrically in the detector 107. More specifically, the conductive leads 108 may be arranged in layers 107A and 107B. Although the layers 107A and 107B are shown as being horizontally disposed in FIG. 2B, each layer in fact represents conductive leads that are vertically disposed concentrically along a height of the device. Although FIG. 2B depicts only two layers of conductive leads, any number of layers may be provided. The conductive leads 108 in one layer, for example layer 107A, may be offset with respect to the conductive leads 108 in another layer, for example layer 107B. Alternatively, the conductive leads of one layer may be arranged in any manner with respect to each other and with respect to the conductive leads of an adjacent layer.

The detector 107 may further comprise a payload material 109 which may be disposed in proximity to the two or more conductive leads 108 that form part of the detector 107. The payload material may be disposed in a region between adjacent layers (e.g. layers 107A and 108A) of conductive leads 108. As previously noted, additional layers of conductive leads may be provided in the detector 107 beyond those depicted in FIG. 2B and the payload material 109 may be provided between each pair of adjacent layers of conductive leads, or in accordance with certain embodiments of the invention, a subset of adjacent layers of conductive leads.

The payload material 109 may be any compound or mixture of compounds that increases soil nutrient content and serves to increase and/or optimize agricultural yields. For example, the payload material may be one or more fertilizers, one or more pesticides, and/or one or more herbicides.

In one or more embodiments of the invention, the biodegradable shell 101 of the device 100 may at least partially degrade in response to the presence and/or occurrence of one or more environmental conditions. The environmental conditions may include at least one of: the presence of one or more chemical compounds in a soil of an environment in which the device is disposed, the presence of one or more chemical compounds in a gaseous atmosphere of the environment in which the device is disposed, decomposition of a mass of the payload material, and a water content of the soil of the environment.

Degradation of at least a portion of the biodegradable shell 101 may cause release of an amount of the payload material 109 enclosed by the shell and included in the detector 107. Release of the amount of the payload material may expose and bring into contact two or more of the conductive leads 108 in the detector.

Figure 2C:
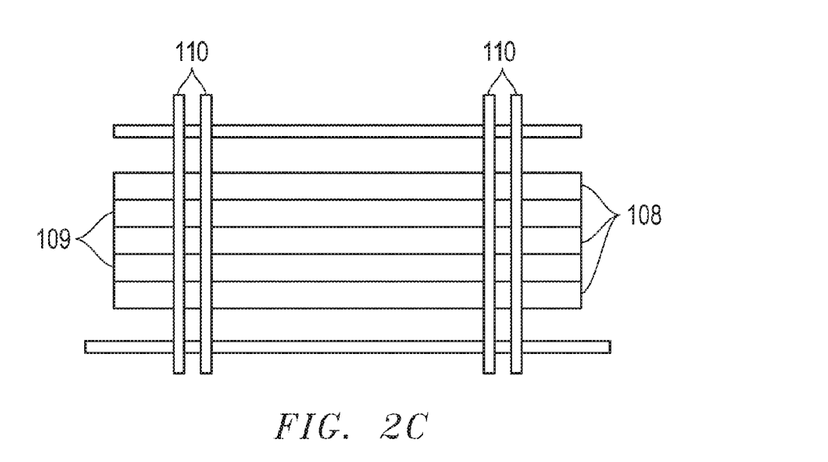
FIG. 2C is a depiction of a portion of the detector of the biodegradable device depicted in FIGS. 1A-1B.

FIG. 2C depicts a view of a portion of the detector of device 100, for example that portion of the detector between the dashed lines in FIG. 1B separated by distance 1. In one or more embodiments, the conductive leads 108 in the detector may be provided under tension such that conductive leads 108 disposed in adjacent layers are urged together under an urging/tension force upon release of the payload material 109 disposed between the adjacent layers of conductive leads. Tension straps 110 may be provided, for example, to provide the necessary tension force between adjacent layers of conductive leads.

Referring to FIGS. 2B and 2C, in one or more embodiments, the detector 107 may communicate release of the amount of the payload material 109 to the device circuitry. Release of payload material 109 disposed between adjacent layers of conductive leads 108 (e.g. layers 107A and 107B) may expose at least a portion of the conductive leads and the exposed leads may be brought into contact with one another via the tension force acting on the leads. Contact between conductive leads completes a communication path between the detector and the device circuitry whereby the circuitry receives a data signal indicating that an amount of the payload material has been released.

Upon receipt of the data signal from the detector indicating that an amount of the payload material has been released, the circuitry may perform a delivery notification operation in which the circuitry controls the antenna to transmit a signal indicating that the device has released an amount of the payload material.

The signal transmitted by the device may have one or more parameters associated therewith that are correlated with an amount of the payload material that has been released. The one or more parameters may be a frequency of the signal and/or an amplitude of the signal. A parameter associated with the signal may be positively correlated to a degree of contact between conductive leads in the detector which may in turn be related to an amount of the payload material that has been released. For example, release of a greater amount of payload material may result in a greater degree of contact between the conductive leads of adjacent layers in the detector. The greater degree of contact between the conductive leads may result in the generation and transmission of a signal as part of the delivery notification operation that has a higher frequency and/or a greater amplitude.

Figure 3:
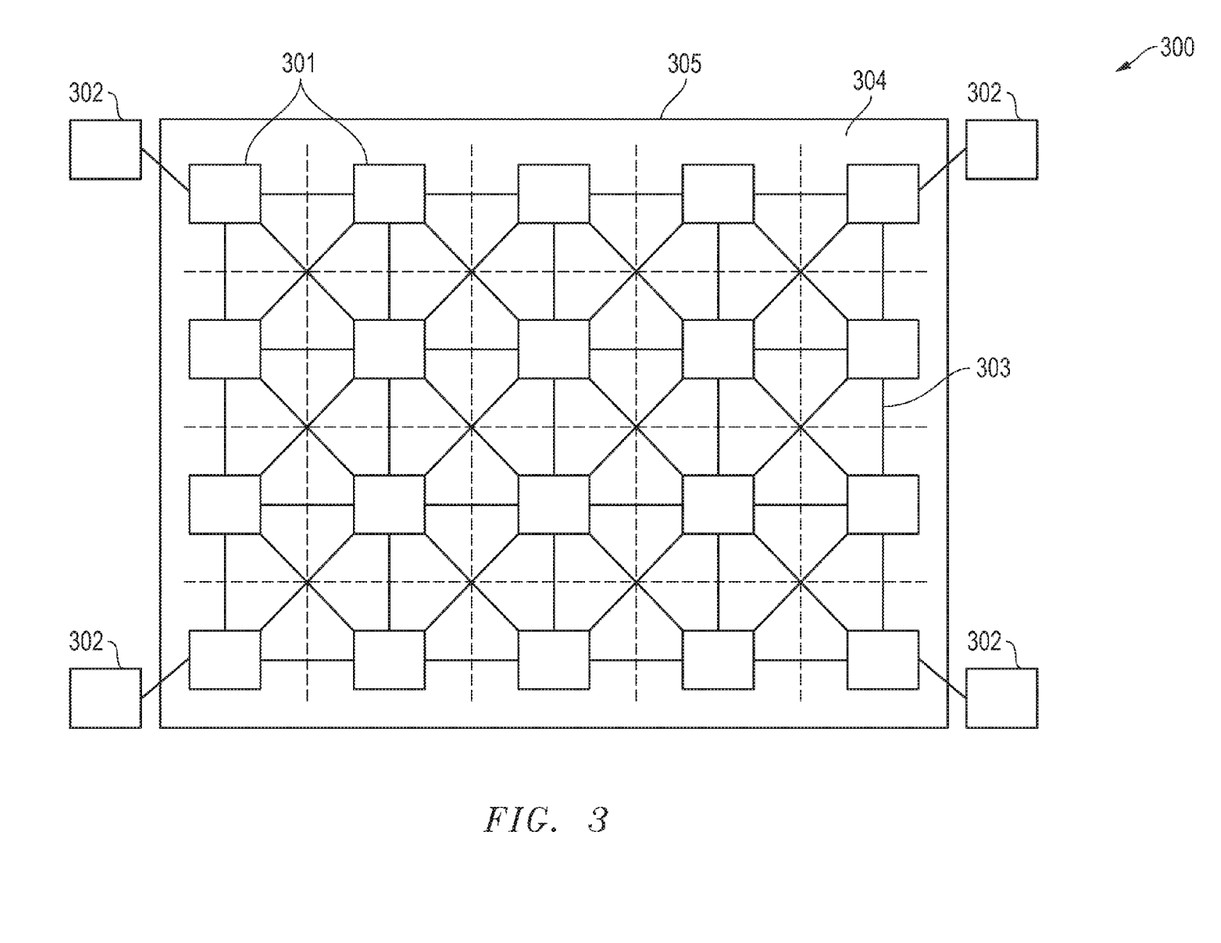
FIG. 3 is a block diagram of a mesh network of biodegradable devices in accordance with an embodiment of the invention.

Referring to FIG. 3, in accordance with one or more embodiments of the invention, a mesh network 300 includes: a plurality of biodegradable devices 301 networked together in accordance with a mesh topology, and one or more edge collection devices 302. Each biodegradable device 301 is capable of communicating with other devices in the network 300 via one or more communication links 303.

In accordance with one or more embodiments of the invention, the mesh network 300 may be a wireless mesh network. The devices 301 in the mesh network 300 may be configured to communicate in accordance with any communications protocol known in the art, including but not limited to IEEE 802.11 wireless communication standards such as 802.11a, 802.11b. 802.11g, 802.11n, 802.11s, and 802.16, cellular technologies, and so forth.

Wireless mesh network architecture eliminates the need for wired connections between devices in the network. Signal strength is maintained in the network by breaking long communication distances into a series of shorter hops between devices. Intermediate devices within a communication path from one device in the network to another device in the network cooperatively and dynamically make routing decisions based on knowledge of the network configuration. As is characteristic of mesh networks generally, failure of any single device in the network 300 does not affect operation of the network. That is, if a single device 301 in the network 300 fails, the network 300 will dynamically reconfigure itself to identify alternate communication paths between the operating devices in the network that do not require transmission through the failed device.

Each biodegradable device 301 may be adapted to respond to one or more environmental conditions in a sector 304 surrounding the device. The collection of sectors 304 together may form an aggregate area 305 with respect to which the devices 301 are capable of generating and transmitting data to the edge collection devices 302. FIG. 3 depicts the edge collection devices 302 as being provided at select intervals along the perimeter of the aggregate area 305. However, the edge collection devices 302 may be arranged according to any number of alternate configurations. Further, FIG. 3 depicts the edge collection devices 302 as being configured to communicate with only select devices 301 of the network 300. However, other network architectures that provide for data communication between the edge collection devices 302 and additional devices 301 within the network 300 are within the scope of the disclosure.

According to one or more embodiments, the aggregate area 305 may represent a plot of land and/or an atmosphere surrounding the plot of land. The plot of land may be an agricultural field, a landscaped piece of land, a lawn of a residence, or any other environment in which the mesh network of biodegradable devices may be disposed. Each sector 304 may represent a subset of the aggregate area 305 and may be associated with a particular device 301. The device associated with a particular sector 304 may be configured to generate and transmit data to the mesh network pertaining to the associated sector 304.

Each biodegradable device 301 in the network 300 may be a biodegradable device in accordance with any of the previously disclosed embodiments. As such, each device 301 may comprise a biodegradable outer shell that degrades upon exposure to one or more environmental conditions present in the sector 304 associated with that device. As previously discussed, the one or more environmental conditions may include at least one of: the presence of one or more chemical compounds in a soil of the sector 304, the presence of one or more chemical compounds in a gaseous atmosphere of the sector 304, decomposition of a mass of the payload material stored in the detector of the device 301, and a water content of the soil of the sector 304.

The biodegradable shells of different devices in the network 300 may degrade at varying rates depending on the particular environmental conditions present in the sectors corresponding to those devices. For example, if the soil of sector A has a higher water content than the soil of sector B, the shell of the device associated with sector A may degrade at a quicker rate than the shell of device associated with sector B. Other conditions that may result in varying rates of shell degradation between devices in the network include, but are not limited to, moisture levels in a gaseous atmosphere of each sector, nutrient saturation levels in each sector, an amount of fertilizer already present in each sector, an amount of chemical runoff in each sector, and so forth.

As described previously, degradation of the outer shell of a device 301 may result in the release of an amount of a payload material stored in a detector of the device. The detector may be adapted to communicate release of the amount of the payload material to circuitry included in the device. More specifically, in accordance with one or more embodiments of the invention, release of an amount of payload material disposed between adjacent layers of conductive leads provided in the detector may expose at least a portion of the conductive leads. The exposed portion of conductive leads may be brought into contact with one another under a tension force acting on the leads. Contact between conductive leads completes a communication path between the detector and the device circuitry whereby the circuitry receives a data signal indicating that an amount of the payload material has been released.

Upon receipt of the data signal from the detector indicating that an amount of the payload material has been released, the circuitry may then perform a delivery notification operation in which the circuitry controls the antenna to transmit a signal indicating that the device has released an amount of the payload material.

As described previously, the signal transmitted by the device may have one or more parameters associated therewith that are correlated with an amount of the payload material that has been released. For example, the one or more parameters may be a frequency of the signal and/or an amplitude of the signal.

In accordance with one or more embodiments of the invention, the device circuitry of each device 301 in the network 300 may be capable of performing, in addition to the delivery notification operation, a signal receive operation in which the circuitry determines that a signal transmitted from another biodegradable device has been received by the antenna of the device, and a signal repeat operation in which the circuitry controls the antenna to re-transmit a signal received from another biodegradable device in the network.

In an embodiment of the invention, a method for collecting payload material delivery data is disclosed. Referring to the flowchart depicted in FIG. 4, the method may comprise, in step S400, establishing a mesh network that includes: a plurality of biodegradable devices and one or more edge collection devices. The mesh network may be the network 300 depicted in FIG. 3. The mesh network may be arranged and configured in accordance with a mesh topology that includes any mesh architecture and network communication protocol known in the art.

Figure 4:
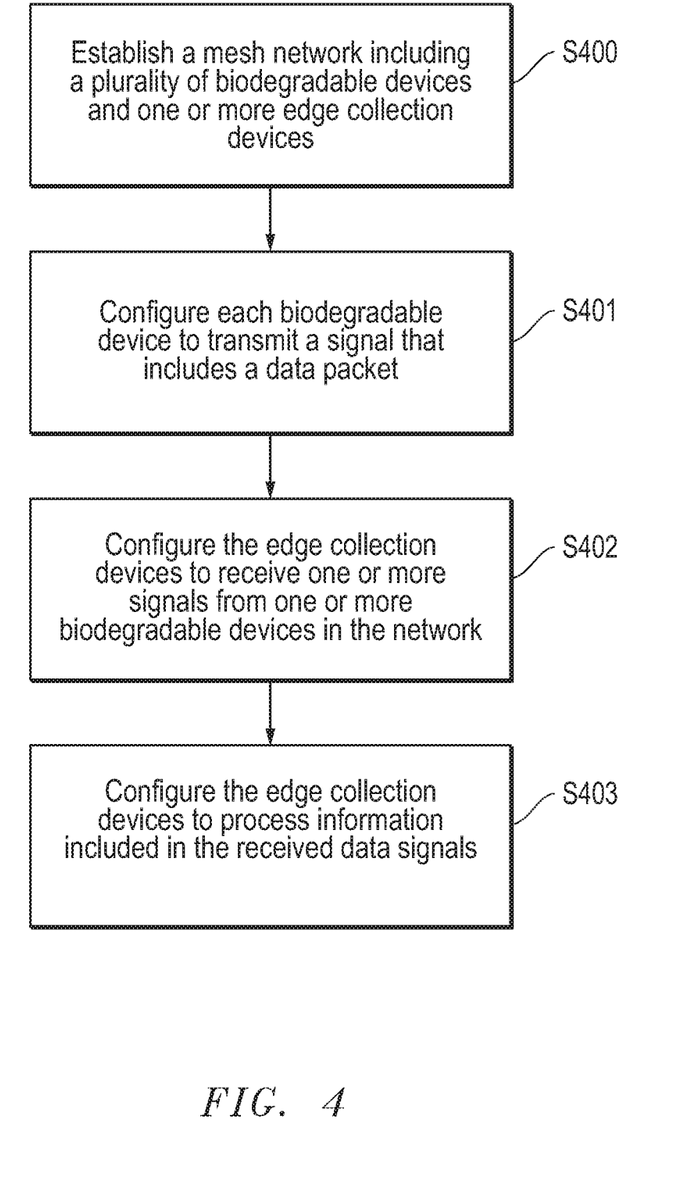
FIG. 4 is a flowchart that depicts a method of establishing and configuring a mesh network of biodegradable devices in accordance with an embodiment of the invention.

In step S401 of the method, each device in the mesh network may be configured to transmit a signal to one or more other biodegradable devices in the mesh network. The signal may comprise a data packet having a plurality of data bits. The plurality of data bits may include a first set of the data bits storing an origin identifier and a second set of the data bits storing one or more hop identifiers. The signal may be transmitted by the device as part of the delivery notification operation, the signal receive operation, and/or the signal repeat operation.

In addition, in one or more embodiments of the invention, each device may be further configured to generate and transmit a repeating keep-alive signal during idle transmission periods. In particular, the circuitry of each device may be further configured to perform a keep-alive operation, in which the circuitry controls the antenna to transmit a keep-alive signal during periods of idle transmission.

The origin identifier may be associated with and may provide information representing a location of a device that released the amount of the payload material and that generated and initially transmitted to the mesh network the signal comprising the data packet as part of the delivery notification operation. Each of the hop identifiers may be associated with and may provide information representing a location of a biodegradable device that received the signal comprising the data packet from another device in the network. The origin identifier and each of the hop identifiers may be any identifier capable of uniquely identifying the device with which it is associated. An identifier that uniquely identifies a device in the network may act as an origin identifier or a hop identifier depending on whether the device generated the signal that comprises the data packet that includes the identifier.

In step S402 of the method, the edge collection devices may be configured to receive one or more signals transmitted from one or more of the plurality of biodegradable devices in the network. Depending on the particular mesh architecture of the mesh network, one or more of the devices in the network may be configured to transmit signals to the edge collection devices.

In step S403, the edge collection devices may be configured to process information included in the signals received from devices in the network. The information that is processed for each signal may include the origin identifier and the hop identifiers included in the data packet contained in the received signal as well as the one or more parameters associated with the received signal which are correlated to an amount of the payload material released by the device associated with the origin identifier.

In one or more embodiments of the invention, the edge collection devices may generate a topographical map of payload material delivery by devices in the network based on the processed information. The topographical map may provide information regarding the relative concentration of payload material delivered by devices in the network. For example, the topographical map may indicate the amount of payload material delivered by each device in the mesh network as a fraction of the total amount of payload material delivered by all devices in the network. Further, the map may provide an indication of relative payload material delivery between devices in the network over a specified period of time. It will be understood by those of ordinary skill in the art that any number of means may be chosen for representing and conveying information regarding the distribution of payload material delivery among devices in the network.

In one or more embodiments of the invention, information provided by the edge collection devices that relates to the relative delivery of payload material between and among the biodegradable devices in a mesh network may allow an entity to take specific targeted actions to effectively optimize agricultural yields. Fertilizers are generally distributed evenly across an agricultural field, a practice which can lead to a non-uniform agricultural yield. In particular, a uniform distribution of fertilizer may result in certain sectors of the field generating a lower yield than other sectors due to a variety of factors such as a reduced concentration of naturally present soil nutrients in those sectors. In response to a non-uniform agricultural yield, conventional practice is to again distribute fertilizer uniformly across the field in subsequent applications. However, this practice often results in overuse of fertilizer, which in turn may lead to adverse environmental effects such as increased chemical runoff.

With information provided by the edge collection devices relating to fertilizer distribution by devices within the mesh network, a farmer may be able to target the application of additional fertilizers to specific sectors of an agricultural field so as to obviate the need for a second uniform distribution of fertilizer across the entire field.

The information provided by the edge collection devices allows a farmer to engage in targeted actions with respect to specific sectors of a field. For example, depending on the nature of the fertilizer delivery information relating to a specific sector, a farmer may decide to use an alternative type of fertilizer in the sector, use an activation agent to enhance the efficacy of fertilizer already present in the sector, and/or apply additional water to activate fertilizer present in the sector.

As an exemplary scenario, the information provided by the edge collection devices may indicate that Device A in Sector A is releasing fertilizer at an acceptable rate, while Device B in Sector B is releasing fertilizer at a significantly slower rate. Sector B generates a lower yield due to the failure of Device B to adequately disperse the fertilizer into the soil. A farmer would thus be informed that it is the lack of effective dispersal and not the efficacy of the fertilizer that has resulted in the lower yield for Sector B. As such, a farmer may be able to take targeted action with respect to Sector B to improve its agricultural yield, such as for example, adding activation agents to Sector B to accelerate the dispersal rate of fertilizer from Device B.

In the scenario presented in the previous paragraph, Device A in Sector A is dispersing fertilizer at an acceptable rate. Therefore, an adequate amount of fertilizer may be present in Sector A which may result in an optimal yield for Sector A. Alternatively, although an adequate amount of fertilizer may be present in Sector A, the yield generated may continue to be sub-optimal. Information provided by the edge collection devices relating to the sub-optimal yield generated in Sector A may inform a farmer: 1) that the mere presence of an adequate amount of fertilizer in Sector A is not sufficient to generate an optimal yield, and 2) that additional secondary measures need to be taken. These secondary measures may include enhanced watering of Sector A and/or the addition of activation agents to improve the efficacy of the fertilizer. If these measures are not successful, it may become evident that the fertilizer being used in Sector A may not be effective for the particular soil conditions in Sector A and alternative types of fertilizer may be used in Sector A in subsequent applications.

In accordance with one or more embodiments of the invention, edge collection devices provide information relating to payload material delivery by biodegradable devices in a mesh network. The information may be used by various entities to take targeted action with respect to specific sectors of an environment in which the mesh network is disposed in order to optimize the delivery of payload material and the yield generated. In this manner, constraints may be imposed on the delivery of payload material and other chemicals in order to enhance growth and minimize the adverse environmental impact of chemical runoff to surrounding water sources.

It should be noted that specific examples are provided above only for purposes of illustration of embodiments of the present invention and are not intended to limit to scope of the present disclosure. Although the examples above involve the delivery of fertilizer to an agricultural field, embodiments of the present invention are not limited to this scenario, as the payload material may be any material known in the art and the payload material may be delivered to any environment.

Figure 5:
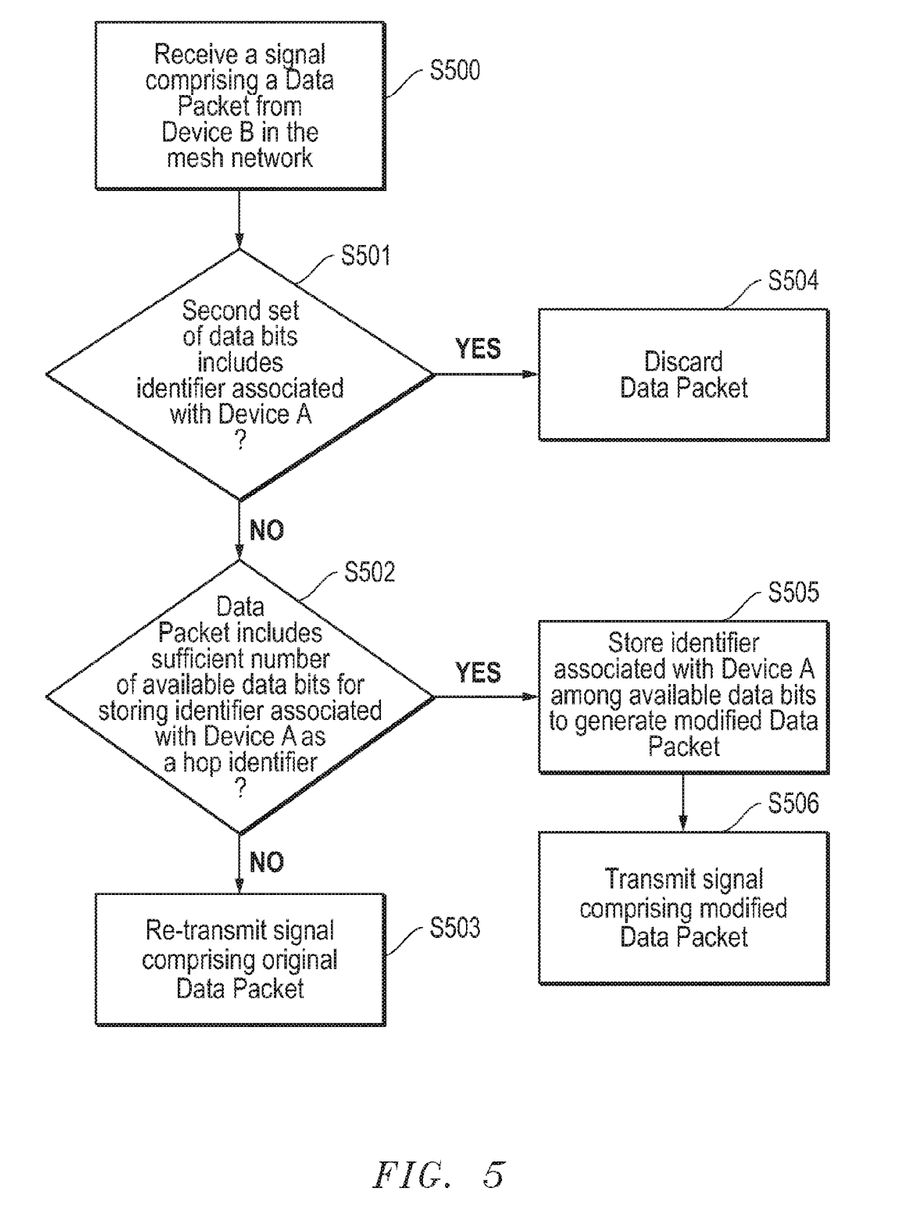
FIG. 5 is a flowchart that depicts a signal receive operation and a signal repeat operation performed by the circuitry of a biodegradable device in a mesh network in accordance with an embodiment of the invention.

As noted previously, the circuitry of each biodegradable device 301 in the mesh network 300 (FIG. 3) may be capable of performing a signal receive operation and a signal repeat operation in addition to the delivery notification operation. FIG. 5 depicts a flowchart that illustrates a signal receive operation and a signal repeat operation performed by the device circuitry in accordance with an embodiment of the invention. In step S500, which may form part of the signal receive operation, the device circuitry of Device A in a mesh network determines that a signal has been received by the antenna of Device A from Device B in the mesh network. The signal may comprise a data packet that includes a plurality of data bits including a first set of data bits storing an origin identifier and a second set of data bits storing one or more hop identifiers.

Steps S501-S506 depict the signal repeat operation in accordance with an embodiment of the invention. In step S501, the device circuitry of Device A makes a first determination as to whether the second set of data bits of the received data packet stores an identifier associated with Device A among the one or more stored hop identifiers. This determination may be made by any means known in the art, for example, by performing a bit-by-bit comparison of each stored hop identifier with the identifier associated with Device A. If, in step S501, it is determined that the second set of data bits stores the identifier associated with Device A, in step S504, the device circuitry of Device A discards and does not re-transmit the data packet.

Alternatively, if it is determined in step S501 that the second set of data bits does not store the identifier associated with Device A among the one or more stored hop identifiers, in step S502, the device circuitry of Device A makes a second determination as to whether the received data packet includes a sufficient number of available data bits for storing the identifier associated with Device A as a hop identifier. If it is determined that the data packet does not include a sufficient number of available bits, the device circuitry of Device A controls the antenna of Device A to re-transmit the original signal received from Device B including the data packet as it was received.

Alternatively, if it is determined in step S502 that the data packet does include a sufficient number of available data bits, the data packet is modified to store the identifier associated with Device A among the one or more hop identifiers (S503). In step S506, the device circuitry of Device A controls the antenna of Device A to transmit a signal that includes the modified data packet (modified to include the identifier of Device A among the hop identifiers) to one or more other devices in the mesh network.

In accordance with the signal repeat operation described above, when a device in the mesh network receives a signal from another device in the network, the signal will not be transmitted if the identifier associated with the device is already stored among the hop identifiers in the data packet of the signal. In this manner, duplicate transmission of signals may be avoided. However, some redundant transmission is possible if a device receives on multiple occasions the same signal having a data packet that does not store the identifier associated with the device among the hop identifiers upon receipt and that does not include a sufficient number of available data bits for storing the device's identifier thereafter.

The transmission of signals in mesh networks of the present invention in accordance with the signal receive and signal repeat operations described above provides for the efficient communication of payload material delivery data between biodegradable devices of the mesh network and ultimately to the edge collection devices of the network, while minimizing redundant data transmissions.

While the present invention may have been described through reference to specific embodiments, the invention is not limited to these specific embodiments as other embodiments and variations are within the scope of the invention.

What is claimed is:

1. A biodegradable payload material delivery and notification device comprising:
   a biodegradable shell enclosing at least a portion of a biodegradable detector, the detector comprising a payload material; and
   biodegradable circuitry electrically connected to the detector and capable of performing a delivery notification operation;
   wherein,
   at least a portion of the biodegradable shell degrades upon exposure to one or more environmental conditions causing release of an amount of the payload material, and
   the detector communicates release of the amount of the payload material to the circuitry causing the circuitry to perform the delivery notification operation, the delivery notification operation comprising generating and transmitting to a mesh network a signal having one or more parameters associated therewith that are correlated with the amount of the payload material released.

2. The device of claim 1, wherein the one or more parameters associated with the signal that is transmitted to the mesh network as part of the delivery notification operation comprise at least one of:
   a frequency of the signal; and
   an amplitude of the signal.

3. The device of claim 1, further comprising:
   a plurality of biodegradable conductive leads,
   wherein,
   the detector comprises two or more of the plurality of conductive leads and is electrically connected to the circuitry via the two or more conductive leads, the payload material being disposed in proximity to the two or more conductive leads,
   release of the amount of the payload material exposes and brings into contact at least a portion of the two or more conductive leads, and
   the circuitry performs the delivery notification operation in response to a signal received from the detector indicating release of the amount of the payload material, the signal being generated upon contact of the at least a portion of the two or more conductive leads.

4. The device of claim 3, further comprising:
   a biodegradable power source connected to the circuitry via one or more of the plurality of conductive leads; and
   a biodegradable antenna connected to the circuitry via one or more of the plurality of conductive leads.

5. The device of claim 4, the circuitry capable of performing one or more additional operations comprising:
   a signal receive operation in which the circuitry determines that a signal transmitted from another biodegradable device has been received by the antenna; and
   a signal repeat operation in which the circuitry controls the antenna to re-transmit a signal received from another biodegradable device.

6. The device of claim 1, wherein the one or more environmental conditions comprise at least one of:
   one or more chemical compounds present in a soil of an environment in which the biodegradable device is disposed;
   one or more chemical compounds present in a gaseous atmosphere of the environment in which the biodegradable device is disposed;
   decomposition of a mass of the payload material; and
   a water content in the soil of the environment.

7. A mesh network comprising:
   a plurality of biodegradable devices networked together in accordance with a network architecture and a network communications protocol; and
   one or more edge collection devices;
   wherein,
   each biodegradable device is configured to transmit a signal to one or more other biodegradable devices in the mesh network, the signal comprising a data packet having a plurality of data bits including:
   a first set of the data bits storing an origin identifier, and
   a second set of the data bits storing one or more hop identifiers; and
   the edge collection devices receive one or more signals from one or more of the plurality of biodegradable devices and process information included in the one or more received signals.

8. The mesh network of claim 7, wherein the edge collection devices generate a topographical map based on the processed information, the map indicating relative concentrations of payload material delivered by biodegradable devices in the mesh network.

9. The mesh network of claim 7, wherein each biodegradable device comprises:
   a biodegradable shell enclosing at least a portion of a biodegradable detector, the detector comprising a payload material; and
   biodegradable circuitry electrically connected to the detector and capable of performing a delivery notification operation;
   wherein,
   at least a portion of the biodegradable shell degrades upon exposure to one or more environmental conditions causing release of an amount of the payload material, and
   the detector communicates release of the amount of the payload material to the circuitry causing the circuitry to perform the delivery notification operation, the delivery notification operation comprising generating and transmitting to the mesh network a signal having a parameter associated therewith that is correlated with the amount of the payload material released.

10. The mesh network of claim 9, wherein:
    the origin identifier is associated with and provides information representing a location of a device that released the amount of the payload material and that generated and initially transmitted to the mesh network the signal comprising the data packet as part of the delivery notification operation, and
    each of the hop identifiers is associated with and provides information representing a location of a biodegradable device that received the signal comprising the data packet from another device in the network.

11. The mesh network of claim 10, each biodegradable device in the network further comprising:

a plurality of biodegradable conductive leads,
a biodegradable power source connected to the circuitry via one or more of the plurality of conductive leads; and
a biodegradable antenna connected to the circuitry via one or more of the plurality of conductive leads,
wherein the circuitry of each biodegradable device in the mesh network is capable of performing one or more additional operations comprising:
a signal receive operation in which the circuitry determines that a signal transmitted from another biodegradable device has been received by the antenna; and
a signal repeat operation in which the circuitry controls the antenna to re-transmit a signal received from another biodegradable device.

12. The mesh network of claim 11, wherein the circuitry of a first device in the mesh network performs the signal repeat operation upon determining, as part of the signal receive operation, that a signal comprising a data packet has been received from a second device in the mesh network, the signal repeat operation comprising:
determining whether a first condition is satisfied, the first condition being satisfied if the second set of data bits of the data packet comprises an identifier associated with the first device among the stored hop identifiers; and
discarding the data packet if the first condition is satisfied.

13. The mesh network of claim 11, wherein if the first condition is not satisfied, the signal repeat operation further comprises:
determining whether a second condition is satisfied, the second condition being satisfied if the data packet comprises a sufficient number of available data bits for storing the identifier associated with the first device as a hop identifier;
wherein if the second condition is satisfied, the method further comprises:
storing the identifier associated with the first device among the available data bits of the data packet to generate a modified data packet; and
transmitting a signal comprising the modified data packet,
wherein if the second condition is not satisfied, the method further comprises:
re-transmitting the signal comprising the data packet.

14. A method for collecting and processing payload material delivery data, the method comprising:
establishing a mesh network comprising:
a plurality of biodegradable devices, and
one or more edge collection devices;
configuring each biodegradable device to transmit a signal to one or more other biodegradable devices in the mesh network, the signal comprising a data packet having a plurality of data bits including:
a first set of the data bits storing an origin identifier, and
a second set of the data bits storing one or more hop identifiers;
configuring the edge collection devices to receive one or more signals from one or more of the plurality of biodegradable devices; and
configuring the edge collection devices to process information included in the one or more received signals.

15. The method of claim 14, further comprising:
generating a topographical map based on the processed information, the map indicating relative concentrations of payload material delivered by biodegradable devices in the mesh network.

16. The method of claim 15, wherein each biodegradable device in the mesh network comprises:
a biodegradable shell enclosing at least a portion of a biodegradable detector, the detector comprising a payload material; and
biodegradable circuitry electrically connected to the detector and capable of performing a delivery notification operation;
wherein,
at least a portion of the biodegradable shell degrades upon exposure to one or more environmental conditions causing release of an amount of the payload material, and
the detector communicates release of the amount of the payload material to the circuitry causing the circuitry to perform the delivery notification operation, the delivery notification operation comprising generating and transmitting to a mesh network a signal having a parameter associated therewith that is correlated with the amount of the payload material released.

17. The method of claim 16, wherein:
the origin identifier is associated with and provides information representing a location of a device that released the amount of the payload material and that generated and initially transmitted to the mesh network the signal comprising the data packet as part of the delivery notification operation, and
each of the hop identifiers is associated with and provides information representing a location of a biodegradable device that received the signal comprising the data packet from another device in the network.

18. The method of claim 17, each biodegradable device in the mesh network further comprising:
a plurality of conductive leads;
a biodegradable power source connected to the circuitry via at least a portion of the plurality of conductive leads; and
a biodegradable antenna connected to the circuitry via at least a portion of the plurality of conductive leads,
wherein the circuitry of each biodegradable device in the network is capable of performing one or more additional operations comprising:
a signal receive operation in which the circuitry determines that a signal transmitted from another biodegradable device has been received by the antenna; and
a signal repeat operation in which the circuitry controls the antenna to re-transmit a signal received from another biodegradable device.

19. The method of claim 18, wherein the circuitry of a first device in the mesh network performs the signal repeat operation upon determining, as part of the signal receive operation, that a signal comprising a data packet has been received from a second device in the mesh network, the signal repeat operation comprising:
determining whether a first condition is satisfied, the first condition being satisfied if the second set of data bits comprises an identifier associated with the first device among the stored hop identifiers; and
discarding the data packet if the first condition is satisfied.

20. The method of claim 19, wherein if the first condition is not satisfied, the signal repeat operation further comprises:
determining whether a second condition is satisfied, the second condition being satisfied if the data packet comprises a sufficient number of available data bits for storing the identifier associated with the first device as a hop identifier,
wherein if the second condition is satisfied, the method further comprises:

storing the identifier associated with the first device among the available data bits of the data packet to generate a modified data packet; and transmitting a signal comprising the modified data packet, wherein if the second condition is not satisfied, the method further comprises:

re-transmitting the signal comprising the data packet.

* * * * *